United States Patent [19]

Müller et al.

[11] 4,210,604
[45] Jul. 1, 1980

[54] PROCESS FOR PREPARING SECONDARY AMINES FROM MIXTURES OF ALIPHATIC ALCOHOLS AND NITRILES

[75] Inventors: Heinz Müller; Adolf Becker, both of Burgkirchen, Fed. Rep. of Germany

[73] Assignee: Hoechst Aktiengesellschaft, Fed. Rep. of Germany

[21] Appl. No.: 926,279

[22] Filed: Jul. 20, 1978

[30] Foreign Application Priority Data

Jul. 25, 1977 [CH] Switzerland .................... 9196/77

[51] Int. Cl.$^2$ .................... C07C 85/06; C07C 85/12
[52] U.S. Cl. .................... 260/583 R; 260/583 H; 260/584 B; 260/584 C
[58] Field of Search .......... 260/583 K, 583 H, 583 R, 260/584 B, 584 C

[56] References Cited

U.S. PATENT DOCUMENTS

| | | | |
|---|---|---|---|
| 2,204,653 | 6/1940 | Bock .......................... | 260/584 C X |
| 2,302,388 | 11/1942 | Hester ........................ | 260/584 C X |
| 2,323,658 | 7/1943 | Hester ........................ | 260/584 B X |
| 2,349,461 | 5/1944 | Pratt et al. .................. | 260/583 K |
| 2,372,624 | 3/1945 | Carpenter .................... | 260/584 C |
| 2,717,270 | 9/1955 | Bindler ....................... | 260/584 B |
| 2,941,967 | 6/1960 | Moller et al. ................ | 260/584 B X |
| 3,478,096 | 11/1969 | Cyba .......................... | 260/584 C X |
| 3,626,011 | 12/1971 | Bordenca et al. ............. | 260/584 C X |
| 4,054,605 | 10/1977 | Watts et al. .................. | 260/584 C X |

FOREIGN PATENT DOCUMENTS

| | | | |
|---|---|---|---|
| 1276046 | 8/1968 | Fed. Rep. of Germany ....... | 260/584 C |
| 2252487 | 5/1974 | Fed. Rep. of Germany ....... | 260/584 C |
| 52-8282 | 3/1977 | Japan .......................... | 260/584 C |
| 894748 | 4/1962 | United Kingdom ............... | 260/583 K |

OTHER PUBLICATIONS

Astle, "Industrial Organic Nitrogen Compounds", pp. 22-25 (1961).

*Primary Examiner*—John Doll
*Attorney, Agent, or Firm*—Connolly and Hutz

[57] ABSTRACT

Secondary amines of the formula

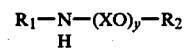

wherein $R_1$ is a straight-chain or branched alkyl, alkenyl or ethylenically multi-unsaturated hydrocarbon radical having from 8 to 26 C atoms, $R_2$ is a straight-chain or branched alkyl, alkenyl or ethylenically multi-unsaturated hydrocarbon radical having from 1 to 26 C atoms, X is an alkylene radical selected from the group $-CH_2CH_2-$, $-CH(CH_3)-CH_2-$, or $-CH_2-CH(CH_3)$, and y is a number from 1 to 20, are prepared from aliphatic nitriles and aliphatic alcohols in the liquid phase in the presence of hydrogenation-dehydrogenation catalysts at elevated temperature. They are valuable intermediates, for example for the manufacture of softeners for textiles, of components for organophilic ammonium bentonites and also of microbiocides, especially for combating bacteria, fungi and algae.

8 Claims, No Drawings

PROCESS FOR PREPARING SECONDARY AMINES FROM MIXTURES OF ALIPHATIC ALCOHOLS AND NITRILES

Secondary aliphatic amines, especially the so-called fatty amines with long carbon chains, are today manufactured in industrial processes essentially by two basic procedures in manifold variations, that is to say by the hydrogenation of corresponding nitriles or by so-called aminolysis or ammonolysis, i.e. the reaction of fatty alcohols with ammonia or primary amines in the presence of hydrogen.

The hydrogenation of long-chain aliphatic nitriles to corresponding secondary amines has been known for a long time. It is carried out industrially under medium to high pressures of about 20 to about 300 bars and at elevated temperatures of about 130° to 260° C. and both two-stage and single stage processes have been developed. The hydrogenation catalysts used are very diverse contact catalysts and contact catalyst systems based on nickel, cobalt and copper chromite, which can optionally be promoted by other metals and frequently are employed in the form of fixed bed contact catalysts. Processes of this type for the manufacture of secondary amines from nitriles are known, for example, from German Pat. No. 963,518, German Pat. No. 1,280,243, German Pat. No. 1,941,290, U.S. Pat. No. 2,781,399, U.S. Pat. No. 2,784,232 and British Pat. No. 836,364.

In addition, the reaction of fatty alcohols with ammonia is gaining in importance for industrial processes. A process of this type is known, in particular, from German Auslegeschrift 2,255,701. In accordance with this process, long-chain fatty alcohols can be converted to the corresponding secondary amines at temperatures of 120° to 250° C. using ammonia in the presence of hydrogen, on hydrogenation/dehydrogenation catalysts and under atmospheric pressure.

Furthermore, from German Auslegeschrift 1,219,493, a process is known, according to which tertiary amines having 6 to 26 C atoms in each aliphatic group are manufactured from mixtures of the corresponding aliphatic alcohols with corresponding nitriles by passing hydrogen through the starting materials, which are in the liquid phase, at temperatures between 160° and 280° C. and under a pressure of between 7 and 14 bars, in the presence of hydrogenation catalysts. Steam and ammonia formed during the reaction are removed from the reaction by the hydrogen which is passed through in excess. Under these conditions, primary and secondary amines can be obtained virtually only in insignificant amounts as by-products.

Finally, from German Auslegeschrift 1,543,317, a process is known in which alcohols and nitriles are reacted in the presence of anhydrous hydrogen fluoride to give amides and these amides are then hydrolyzed in the presence of hydrolyzing agents to give mixtures of carboxylic acids and amines. If only because of the involved isolation of the pure amine from the hydrolysis mixture, this process hardly comes into consideration for the industrial manufacture of fatty amines.

Secondary amines with long C chains are of great technical interest, especially in respect of the further processing thereof to the corresponding quaternary ammonium salts and the use thereof as softeners for textiles. On the other hand, particular difficulties are always encountered when manufacturing these amines by the various processes, since, in the reaction chain primary amine-secondary amine-tertiary amine, it is relatively easy to obtain the initial stage or the final stage but considerably more difficult to obtain the intermediate stage, that is to say the secondary amine, in high yields. There was, therefore, a need to use the technically interesting reaction of fatty alcohols with fatty nitriles for the manufacture of secondary fatty amines also.

It has now been found that this is possible with a process for the manufacture of secondary aliphatic amines from aliphatic nitriles and aliphatic alcohols in the liquid phase, by passing hydrogen through the reaction mixture, in the presence of hydrogenation/dehydrogenation catalysts, at elevated temperatures and with removal of the water of reaction, which comprises bringing aliphatic alcohols of the formula

$R_1OH$ in which $R_1$ denotes a straight-chain or branched, but in the α-position at most singly branched, alkyl, alkenyl or ethylenically multi-unsaturated hydrocarbon radical having 8 to 26 C atoms or an alkoxyalkyl radical of the formula $R_2(OX)_m$— with a molecular weight of at least 130, in which $R_2$ is a straight-chain or branched alkyl, alkenyl or ethylenically multi-unsaturated hydrocarbon radical having 1 to 26 C atoms, X is a radical —$CH_2CH_2$—, —$CH(CH_3)$—$CH_2$— or —$CH_2$—$CH(CH_3)$— and m is an integer or fraction between 1 and 20 and, within m, combinations of the radicals X can be present, or mixtures of such alcohols into intimate contact, at temperatures of 120° to 260° C. and under conditions of virtually atmospheric pressure with aliphatic nitriles of the formula

$R_3$—CN in which $R_3$ denotes a straight-chain or branched alkyl, alkenyl or ethylenically multi-unsaturated hydrocarbon radical having 8 to 26 C atoms or the radical of an ether-nitrile of the formula $R_4$—$(OX)_n$—$O(CH_2)_p$— with a molecular weight of at least 130, in which $R_4$ is a straight-chain or branched alkyl, alkenyl or ethylenically multi-unsaturated hydrocarbon radical having 1 to 26 C atoms, X is a radical as defined above, n is an integer or fraction between 1 and 20, or zero, and p can be 1 or 3 and, within n, combinations of the radicals X can be present, or with mixtures of such nitriles, in a molar ratio of alcohol:nitrile of 90:10 to 10:90, with at least 2 moles of hydrogen per mole of nitrile, an ammonia concentration of between 3 and 75% by volume being maintained in the reaction gas during the entire reaction time.

The term ethylenically multi-unsaturated hydrocarbon radical is to be understood as radicals having up to 5, preferably up to 3 double bonds, which are not cumulated.

Starting materials which may be mentioned for the process according to the invention are, on the one hand, aliphatic alcohols of the formula

$R_1$—OH in which $R_1$ represents an alkyl radical or an ethylenically unsaturated hydrocarbon radical with one or more double bonds, which has a total of 8 to 26 C atoms. Such alcohols can have one or more chain branches in the chain, in the form of secondary or tertiary C atoms, but they have at most one branch in the α-position relative to the OH group, that is to say they are primary or secondary alcohols. The following may be mentioned merely by way of example: n-octyl alcohol, 2-ethylhexanol, isooctyl alcohol, isononyl alcohol, lauryl alcohol, isotridecyl alcohol, oleyl alcohol, cetyl alcohol and stearyl alcohol. Alcohols or mixtures of alcohols which are formed by the hydrogenation of natural fatty acids or fatty acid esters are also suitable, such as, for example, tallow fatty alcohol or palm kernel fatty alcohols. These also include unsaturated alcohols with one or more double bonds which are formed by the hydrogenation of the multi-unsaturated fatty acid esters of fish oil fatty acids and rapeseed oil fatty acids. The inexpensive primary alcohols having up to 24 C atoms which are obtained by a growth reaction of ethylene in accordance with the Ziegler process may also be mentioned. Alcohols which are branched to a greater or lesser extent, such as are manufactured by oxo syntheses from straight-chain or branched centrally or terminally unsaturated olefins, or isooctadecyl alcohol which is accessible from isononyl aldehyde can also be used as starting alcohols. Secondary alcohols which can be used are, for example, those which are accessible by the known processes of direct oxidation of straight-chain and branched paraffins in the presence of boric acid. The starting alcohols can be in the form of any desired mixtures. Straight-chain and branched primary alcohols, which can be saturated or unsaturated by 1 to 2 ethylenic double bonds and which have 14 to 22 and especially 16 to 18 C atoms, are preferred.

Ether-alcohols, such as are formed by oxethylation and/or oxpropylation of primary and secondary alcohols are also suitable as starting alcohols in the process according to the invention. In these ether-alcohols, the radical $R_1$ assumes the meaning $R_2(OX)_m$—. The units X can be units derived exclusively from ethylene oxide or propylene oxide or can also be mixtures of such units, specifically in a statistical distribution or in the form of blocks. m denotes the average degree of oxalkylation. Therefore, m can be either an integer or a fraction, which for the starting alcohol component of the process according to the invention is between 1 and 20, preferably between 1 and 8 and especially between 1 and 3. $R_2$ can be a straight-chain or branched alkyl, alkenyl or ethylenically multi-unsaturated hydrocarbon radical having 1 to 26, preferably 8 to 22, C atoms, but with the proviso that the molecular weight of the total radical $R_2(OX)_m$— must be at least 130, since only with such radicals is the vapor pressure of the alcohol, under the reaction conditions of the process according to the invention, sufficiently low to prevent the starting alcohol being removed from the process with the water of reaction. The said ether-alcohols can also by employed as a mixture with the abovementioned straight-chain or branched, saturated or unsaturated, primary or secondary alcohols.

The second reactant in the process according to the invention comprises nitriles of the formula $R_3CN$ in which the radical $R_3$ can likewise represent an alkyl radical or an ethylenically unsaturated hydrocarbon radical with one or more double bonds, but in this case, in contrast to the starting alcohols, a tertiary C atom can also be present in the α-position. In other respects, what has been stated for the radicals $R_1$ in the starting alcohols applies in respect of the chain branching in $R_3$.

These radicals $R_3$ have 8 to 26 C atoms. Preferred nitriles are straight-chain and branched saturated nitriles, or those with up to 3 ethylenic double bonds, which have 14 to 22, especially 16 to 18, C atoms. The starting nitriles also can be employed in the form of any desired mixtures within the stated limits.

The nitriles required as starting components in the process according to the invention are manufactured in accordance with known processes from the carboxylic acids with the same chains, by reaction with ammonia under dehydrating conditions. Such nitriles are also accessible by the so-called ammonoxidation of hydrocarbons or by the conversion of alcohols to nitriles with ammonia, which preferably takes place on iron contact catalysts.

Ether-nitriles are also suitable as starting nitriles and the radical $R_3$ then assumes the meaning $R_4$—$(OX)_n$—$O(CH_2)_p$—, in which $R_4$ can be a straight-chain or branched alkyl, alkenyl or ethylenically multi-unsaturated hydrocarbon radical having 1 to 26 C atoms and preferably having 8 to 22 C atoms. (OX) in this case also are units which are formed by oxalkylation with ethylene oxide and/or propylene oxide and which again, when both oxalkylate radicals are represented, can be statistically distributed or in the form of block copolymers. The degree of oxalkylation n can assume the same values as m in the starting ether-alcohols, but in the case of the ether-nitriles can also be nought. Finally, the index p can be 1 or 3. The ether-nitriles are also subject to the proviso that the total radical $R_4$—$(OX)_n$—$O(CH_2)_p$— should have a molecular weight of at least 130. The said ether-nitriles can be prepared by known processes, for example those nitriles in which p=1 can be prepared by reacting chloromethyl ethers with copper cyanide, and the corresponding chloromethyl ethers, in turn, can be obtained by reacting alcohols or oxalkylated alcohols with formaldehyde and HCl. Ether-nitriles in which the index p is 3 can be obtained via the corresponding etheralcohols, which, in turn, can be prepared by reacting alcohols or oxalkylated alcohols with oxetane (1,3-propylene oxide).

The nitriles and/or ether-nitriles which can be employed within the abovementioned limits can also be present in the form of mixtures.

The starting alcohols and the starting nitriles are in the liquid phase during the reaction.

The reaction within the scope of the process according to the invention takes place under conditions of atmospheric pressure, that is to say under virtually normal pressure. Slight rises in pressure to about 0.5 to 1 bar of excess pressure, which result, for example, from resistances in the lines and also from overcoming the liquid level as a result of the gases being passed in, are considered here to be in the region of virtually atmospheric pressure, as is a slight reduced pressure, which can result, for example, from a small pressure difference in the gas circulating pump on the suction side of the apparatus.

The temperature during the reaction according to the process of the invention should be between about 120° and about 260° C., and, in order to achieve economic rates of reaction, the reaction is preferably carried out in a temperature range between about 180° and about 260° C. However, even in the latter range, a perceptible conversion to the desired secondary amines already takes place at the temperatures below this range, above 120° C., which temperatures in some cases are deliberately to be passed through slowly.

The catalysts required for the process according to the invention are those with a hydrogenating and a dehydrogenating function. These are preferably nickel catalysts, which can be either in the form of the active Raney nickel types or in granular or powder form, with or without support material. Further suitable catalysts are the corresponding cobalt catalysts or nickel/cobalt or nickel/cobalt/copper mixed catalysts, and also copper chromite catalysts, which can optionally be provided with additives of copper oxide, alkali metals or alkaline earth metals, such as, in particular, barium. Particularly suitable catalysts for the process according to the invention are nickel and cobalt catalysts of very diverse types, with and without additives of other metals and also with supports and activators. Additives and supports which may be mentioned are manganese, iron oxide, zinc oxide, aluminum silicates, aluminum oxide and also $SiO_2$ in the form of kieselguhr or in the form of a synthetic fine powder obtained by a blowing process. The nickel catalysts are preferred.

Pure noble metal catalysts based on palladium and platinum are not very suitable but can be rendered usable by combining them with dehydrogenation contact catalysts, such as, for example, Raney copper or copper/chromium catalysts. In principle, it is possible by such mixing processes to admix two different commercially available contact catalysts in such a way that the desired hydrogenation/dehydrogenation properties are obtained.

The preferred temperature range for the process according to the invention to a certain extent depends on the nature of the catalyst. When nickel catalysts are used, the temperature range from 180° to 200° C. has proved particularly advantageous. The temperature can readily be adjusted to these values, especially in the case of highboiling starting alcohols and starting nitriles with more than about 12 C atoms. In the case of reactants with shorter chains, it is not immediately possible to adjust the temperature to an optimum value above about 180° C. In this case, the reaction is started at 120° C. and initially a relatively small amount of the reaction gas is passed into the nitrile/alcohol mixture. The conversion to high-boiling secondary amines or their precursors already starts at this temperature. As the reaction proceeds, both the temperature and the amount of gas can then be increased slowly.

If the somewhat less active copper/chromium catalysts are used in place of nickel catalysts, the optimum reaction temperature is about 230° to 250° C. In this case, the temperature of nitrile/alcohol mixtures with more than about 15 to 16 C atoms or those with approximately identical boiling points or corresponding vapor pressures can be adjusted immediately to the reaction temperature, without having to pass through a slow heating up period in this case.

As well as depending on the type of contact catalyst, the amount of catalyst for the process according to the invention is, inter alia, dependent on the reaction temperature chosen. Within the process according to the invention, it varies within limits between 1 and 6% by weight, based on the amount by weight of the reactants and calculated relative to active metal or metal oxide. When, for example, approximately equimolar mixtures of alcohols and mixed $C_{16}/C_{18}$ nitriles were used, the required amount of Raney nickel catalyst was, under otherwise identical conditions, 5% by weight at 180° C., 2% by weight at 200° C. and 1% by weight at 210° C. Side reactions were discernible to a slight extent at 210° C. The figures given apply in the case of the once-only use of a fresh contact catalyst.

During the reaction, the reaction mixture is to be provided with at least two moles of hydrogen per mole of nitrile; an excess of hydrogen, which can be as large as desired, is not troublesome. In particular, the amount of hydrogen which in some cases is required for the hydrogenation of ethylenically unsaturated double bonds in the starting nitriles or alcohols must also be taken into account. The reaction mixture must be provided with hydrogen from the start, since undesired side reactions otherwise take place.

The hydrogen concentration present in the reaction gas is calculated from the ammonia concentration, mentioned further below, as the difference between the latter and 100%. Here and in the text which follows, the reaction gas is understood as meaning only the sum of hydrogen and ammonia.

A decisive factor for the reaction of alcohols and nitriles to give secondary amines by the process according to the invention is that not only hydrogen but also ammonia is present in the reaction gas during the entire reaction time. Therefore, care must be taken that the ammonia does not escape in an uncontrolled manner, since a deficit of ammonia decisively impairs the yield of secondary amine. Depending on the molar ratio of the reactants used, the ammonia concentration in the reaction gas can be between 3 and 75% by volume. It can either be kept constant within this range during the entire reaction time or can vary within these limits. The said limits can, in particular, be exceeded briefly and in some cases the concentration can also fall slightly below these limits. However, it is decisive that the ammonia concentration is so regulated that it is kept essentially within these limits during the reaction period. If the ammonia concentration in the reaction gas falls below the limit, provision must be made for increasing the ammonia concentration, and if it exceeds the limit, provision must be made for lowering the ammonia concentration. This applies both for amounts of ammonia which are supplied or removed from outside and for those which are formed from the reactants themselves.

The proportion of the alcohol and nitrile reactants in the process according to the invention can vary within wide limits, up to about a molar ratio of alcohol:nitrile of between 90:10 and 10:90. A molar ratio of alcohol:nitrile of between 70:30 and 30:70 is preferred and the reaction between equimolar amounts of both reactants is particularly preferred; in this context, equimolar, in respect of the given technical data (for example the purity and the homogeneity of the starting materials), is to be understood as meaning a molar ratio of alchol:nitrile of between 60:40 and 40:60. For this latter case, the ammonia concentration should vary between about 3 and 60% by volume and preferably between 3 and 50% by volume. Advantageously, the ammonia concentration should remain more in the lower part of the range when there is a large excess of nitrile and more in the upper part of the range when there is a large excess of alchol. In the latter case, there is also the proviso that, in total, at least an amount of ½ mole of ammonia must be provided per mole of excess alcohol.

Under the conditions of the process according to the invention and depending on the molar ratios of the nitrile and alcohol starting components employed, the gas speed with which the reaction gas, which optionally includes inert gas, passes through the liquid phase or comes into intimate contact therewith should vary between 200 and 600 l of gas per kg of reactant mixture and per hour. These limits are not absolutely critical but the reaction proceeds more slowly at lower gas speeds of, say, 50 to 100 l per kg and per hour. On the other hand, amounts of gas above 600 l per kg and per hour have advantages only when provision is made to enable the larger amounts also to be optimally finely distributed in the liquid phase. Above 1,000 l per kg and per hour, limits are placed on the amount of gas mainly in respect of the technical feasibility and the economy. The intimate contact between liquid, gas and catalyst which is necessary for the reaction is usually produced by directly passing in or circulating the gas with very good stirring or circulation of the liquid phase with the suspended contact catalyst. Jet reactors are particularly advantageous for circulation of this type. In these reactors, the liquid reaction material is intimately mixed in a jet nozzle with the catalyst and the reactive gases, by which means a particularly rapid reaction takes place. The jet nozzle simultaneously provides for circulation of the gas phase and for separation of the water of reaction outside the kettle. As large an amount of gas as possible is also of great importance for rapid and problem-free discharge of the water of reaction formed. In order to accelerate the discharge of the water of reaction and for reasons of cost saving, the reaction gas, that is to say the mixture of hydrogen and ammonia, can be diluted with proportions of inert gases, such as nitrogen or methane. Inert gases can be present in the gas mixture, in addition to the reactive gases hydrogen and ammonia, in proportions of 0 to 50% by volume. It is true that gases of this type lower the partial pressures of hydrogen and ammonia but, on the other hand, they promote the important discharge of the water of reaction.

The reaction can be carried out either by the so-called "open" procedure or by the so-called "closed" procedure. The "open" procedure comprises passing hydrogen through the reaction vessel, which is charged with the reaction mixture of alcohol and nitrile and at the same time contains the catalyst, at the requisite reaction temperature, whilst stirring well, the amount of ammonia necessary to maintain the ammonia concentration in the reaction mixture also being supplied if required. The outlet of the apparatus is via a descending condenser, which advantageously contains a receiver for collecting the water of reaction and is open to the atmosphere. The excess reaction gases leave the apparatus via an off-gas line.

The "closed" procedure, which can also be termed a gas circulation procedure, is the preferred embodiment of the process according to the invention. In respect of the apparatus, it differs from the so-called "open" procedure in that, after the water of reaction has been condensed out by means of a high efficiency condenser, hydrogen and ammonia are cycled via a circulating pump. Hydrogen and ammonia are fed into the apparatus to replenish the amounts consumed. With the "closed" procedure, therefore, equally high yields of secondary amines are obtained with substantially smaller amounts of the two gases. The loss of ammonia can also be kept particularly low when the temperature of the water of reaction separated off is advantageously adjusted to about 90° C. and the gases which are drawn off can condense through a reflux condenser. When this measure is taken, a 1 to 3% strength by weight ammonia solution is obtained in place of approximately 10% strength by weight aqueous ammonia.

With the gas circulation procedure it can prove advantageous to withdraw a specific amount of gas from the cycle, once or repeatedly, that is to say batchwise, during the process or continuously, and to feed in fresh gas as a replacement. In this way, the enrichment of undesired gases, such as are formed in small amounts by side reactions, can be prevented. The withdrawal and feed of the gases can be used both to regulate the ammonia and hydrogen concentrations and also the inert gas concentration. The apparatus for the gas circulation procedure of the process according to the invention also possesses, in addition to the condenser, a device which can be switched on and with the aid of which excess ammonia present in the circulating gas can be completely or partially removed.

The device for regulating the ammonia is advantageously located in the by-pass of the gas cycle of the apparatus. It is actuated as soon as the desired ammonia concentration is exceeded. The said device can be, for example, a wash tower or stirred vessel filled with liquid absorbent or an adsorption tower filled with solid adsorbents.

The adsorbent for ammonia in the said device can be, for example, water or aqueous sulfuric acid. Concentrated sulfuric acid can also be used and this is sprayed in, as needed, in metered amounts at a specific point in the gas cycle.

The monitoring of the ammonia concentration in the reaction gas is carried out, for example, with the aid of an infra-red analyzer or a process chromatograph or with the aid of any other continuous analyzer which supplies analytical data by chemical or physical methods. The analyzer employed can advantageously automatically regulate the feed and withdrawal of ammonia.

After lowering the ammonia concentration by the said measures, it is necessary to replenish the withdrawn amount of gas by hydrogen, optionally as a mixture with inert gases, in the cycle.

As a particularly advantageous measure, the ammonia concentration can be adjusted by a cooling unit which can both withdraw ammonia from the cycle and release ammonia to the cycle. A unit of this type can be installed either in the main cycle or in a secondary cycle.

In the case of the so-called open procedure, a device for regulating the ammonia is superfluous, because in this case the gases are fed direct and in the correct composition into the apparatus. With both the open procedure and the gas circulation procedure, it is important that the water formed is removed rapidly from the liquid reaction phase and that the amount condensed out can be measured in a receiver. The amount of water separated off and the uptake of hydrogen are a measure of the progress of the reaction. The end of the reaction in accordance with the process of the invention can be determined with the aid of the titratable alkalinity of the desired secondary amine.

The procedures have been described from the point of view of a batch process. However, it is also possible to carry out the process according to the invention as a completely or partly continuous process, for example in a tube system in several reactors connected one behind the other or in reaction kettles arranged as a cascade.

Within the process according to the invention, unsaturated nitriles and alcohols can also be used, as already mentioned above. The unsaturated alkyl chains can contain either one or more double bonds. Examples which may be mentioned are oleyl alcohols with iodine numbers of 50 to 95, tallow fatty nitrile with an iodine number of about 50 and also the nitriles of fish oil fatty acids and rapeseed oil fatty acids with iodine numbers greater than 100, and also oleyl nitrile and soya oil nitrile. The process can be so controlled that both saturated and the corresponding unsaturated or partially unsaturated secondary amines are obtained. Copper/chromium catalysts are the most suitable for retaining the double bonds. Unsaturated or partially unsaturated secondary amines can also be obtained from unsaturated nitriles and alcohols using nickel catalysts. In this case, a reaction gas which, in addition to hydrogen, contains about 10 to 60, preferably 20 to 50,% by volume of ammonia is particularly advantageous.

Saturated secondary amines are obtained from unsaturated starting components most advantageously when the ammonia content of the reaction gas varies in the lower region of the indicated limits and when the reaction gas is replaced by pure hydrogen after the formation of the secondary amine has ended. If desired, the temperature can be raised and the amount of gas increased.

The process according to the invention for the formation of the secondary amine usually takes 1.5 to 4, preferably 2 to 3, hours. For the complete hydrogenation of double bonds which are present, approximately the same time again is required in the extreme case (in the case of a high iodine number). The subsequent hydrogenation phase can be shortened if the reaction is carried out under elevated pressure, say at 4 to 10 bars.

The yield of amines, calculated as percentages by weight, obtained by the process according to the invention is about 90 to 99% and in most cases more than 95%, that is to say it is virtually quantitative. The difference consists of non-amine constituents, in particular small amounts of degradation products of the starting alcohols and nitriles, and also impurities in the case of technical grade starting materials. The proportion of the desired secondary amines is 80 to 95 mole % and in most cases more than 90 mole %, based on a total yield of amines of 100 mole %. The remainder comprises primary and tertiary amines, primary amines frequently being completely absent. The color quality of the resulting secondary amines is very good. Iodine color numbers of 0.5 to 2 units (iodine color numbers according to DIN Standard 6,162) are obtained with certainty.

In general, the resulting secondary amines require no special purification process, by a distillation or absorption method, for further processing.

It was known that the hydrogenation of nitriles to secondary amines could be carried out satisfactorily only under medium to high pressures. Therefore, it is to be regarded as surprising that the reaction of alcohols and nitriles in changing molar ratios can be carried out under atmospheric pressure and nevertheless gives high yields of the desired secondary amines. However, slight excess pressure can also be employed in the process according to the invention.

The secondary amines which can be prepared by the process according to the invention are, above all, valuable intermediates. They are preferably used for the manufacture of softeners for textiles, of components for organophilic ammonium bentonites and also of microbiocides, especially for combating bacteria, fungi and algae. Furthermore, they are used for the manufacture of antistatic agents, conditioning and preparation auxiliaries, for hair cosmetics and for synthetic fibers. Secondary amines having a total number of more than 20 C atoms can also be used for the liquid extraction of metals, such as, for example, tungsten, in strongly acid solutions.

The secondary amines which can be manufactured by the process according to the invention can be classified, in respect of the two radicals bonded to the nitrogen atom, as symmetrical secondary amines (both radicals consist of a pure hydrocarbon radical or of a hydrocarbon radical containing ethoxy and/or propoxy groups) and unsymmetrical secondary amines (one radical consists of a pure hydrocarbon radical and the other of a hydrocarbon radical containing ethoxy and/or propoxy groups).

Whilst the symmetrical secondary amines are known (compare German Pat. Nos. 1,280,243 and 1,941,290 and also German Offenlegungsschrift 2,555,895), the unsymmetrical secondary amines, which are likewise obtained by the process according to the invention, have not been described hitherto.

The invention therefore also relates to secondary amines of the formula I

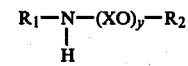

in which $R_1$, $R_2$ and X are as defined and y is a number from 1 to 20.

Preferably, the unsymmetrical secondary amines according to the invention correspond to the formula I in which $R_1$ is a straight-chain or branched alkyl, alkenyl or at most tri-ethylenically unsaturated hydrocarbon radical having 8 to 22 C atoms, $R_2$ is a straight-chain or branched alkyl, alkenyl or at most tri-ethylenically unsaturated hydrocarbon radical having 1 to 22 C atoms, X is the radical $-CH_2-CH_2-$ and y is a number from 1 to 10, especially from 1 to 5.

Amines of particular interest are those unsymmetrical secondary amines of the formula I in which $R_1$ and $R_2$ (identical or different) represent branched or preferably straight-chain alkyl radicals, and in particular $R_1$ is an alkyl radical having 8 to 22 C atoms and $R_2$ is an alkyl radical having 4 to 22 C atoms, and X and y are as defined above. These compounds thus correspond to the formula alkyl($C_8$–$C_{22}$).NH.($CH_2$.$CH_2$.O)$_{1-10}$.alkyl(-$C_4$–$C_{22}$).

These compounds can be isolated from the products of the process according to the invention by fractional distillation or, in the case of boiling points which lie close together, by extractive distillation.

The secondary amines, according to the invention, of the formula I are preferably used for the manufacture of the corresponding quaternary ammonium salts, which have valuable properties as textile auxiliaries.

In the text which follows the invention is illustrated by examples:

EXAMPLE 1

The apparatus consists of a reaction flask which is provided with a gas inlet, with a stirrer and contact thermometer and with a Raschig column which can be heated up to 90° C. A water separator is installed on this column and, if needed, can likewise be heated up to 90° C. if the concentration of the dissolved ammonia in the water of reaction separated off is to be kept as low as possible. A good high efficiency condenser is located on the water separator. An absorption vessel containing 1 Normal sulfuric acid, in which ammonia which has been withdrawn can be detected by titration, is connected to this condenser. The reaction gas in the apparatus is cycled via a circulating pump. Hydrogen required for the reaction is fed into the cycle in such a way that an excess pressure of up to 0.1 bar can prevail in the apparatus. Off-gas can be withdrawn at the outlet of the apparatus. The $H_2SO_4$ absorption vessel can be switched so that the circulating gas can be passed over it, either in total or in the by-pass of the cycle. It is also possible to carry out the absorption of ammonia outside the circulating gas in the offgas in a $H_2SO_4$ absorption vessel.

280.0 g=1.00 mole of stearyl nitrile (N content 5% by weight by the Kjeldahl method) and 186.6 g=0.71 mole of stearyl alcohol (OH number=214) are initially introduced into the apparatus just described. This corresponds to a proportion of 58.5 mole % of nitrile in the reaction mixture. 23.3 g=5% by weight (based on the mixture of the reactants) of a nickel catalyst on a support with 55% by weight of nickel are then added and the apparatus is flushed with nitrogen. After the nitrogen has been displaced by hydrogen, the outlet of the apparatus is closed and the circulating pump is switched on. The system is run with 300 l of circulating gas/kg·hour. After heating up to 200° C., the batch is run for 3 hours at this temperature and during this time 52.6 l of hydrogen are passed in. After withdrawing 2 l of off-gas, the ammonia concentration in the circulating gas is kept in the range between 3 and 25% by volume. After the reaction has ended, the product in the stream of circulating gas is allowed to cool to 100° C. and the apparatus is flushed with nitrogen. A total of 0.131 mole of ammonia is collected in the sulfuric acid receiver in the off-gas line. The resulting water of reaction (16.3 g) contains a further 0.023 mole of ammonia. The contents of the flask are then filtered through Kieselguhr on a suction filter at about 80° C. 96.3% by weight total yield of amine with an amine number of 17.40 is obtained. The amine comprises 92.1 mole % of secondary amine; the remainder is tertiary amine; primary amine was not found.

EXAMPLE 2

280.0 g=1.00 mole of stearyl nitrile (N content 5% by weight by the Kjeldahl method), 262.0 g=1.00 mole of stearyl alcohol (OH number=214) and 27.0 g (=5% by weight based on the mixture of the reactants) of a nickel catalyst on a support (Ni content 55% by weight) are initially introduced into the circulation apparatus described in Example 1. After flushing with nitrogen and displacing the nitrogen by hydrogen, the system is run with 300 l of circulating gas/kg·hour, as described in Example 1. The mixture is heated to 200° C. and the batch is run for 2½ hours and during this time 50.6 l of hydrogen and, from a cold trap, 2.78 g=0.163 mole of ammonia are fed into the cycle, by which means the ammonia concentration is kept in the range of 12 to 27% by volume during the reaction time. Working up is carried out as in Example 1. 20.1 g of water of reaction, which contain 0.034 mole of ammonia, are obtained. A further 0.147 mole of ammonia is collected in the absorption vessel in the off-gas line. A total amine yield of 97.3% by weight with an amine number of 17.73 results. The product is free from primary amine; it contains 96.6 mole % of secondary amine and 7.4 mole % of tertiary amine.

EXAMPLE 3

148.3 g=0.969 mole of decane nitrile (corresponding to 74.8 mole % of nitrile in the mixture), 51.7 g=0.327 mole of decyl alcohol and 10.0 g of a supported nickel catalyst (55% of nickel; 5% by weight based on the mixture) are intially introduced into the apparatus according to Example 1.

After flushing with nitrogen and filling the apparatus with hydrogen, the amount of circulating gas is adjusted to 500 l of circulating gas/kg·hour and the apparatus is heated to 180° C. The batch is run for 5½ hours at this temperature and during this time 58 l of hydrogen are fed in. The circulating gas contains 6% by volume of ammonia when the reaction temperature of 180° C. is reached and contains 20% by volume after ½ hour and 34% by volume after 1 hour. Off-gas is now withdrawn via the $H_2SO_4$ absorption unit in the off-gas line and by this means the ammonia level is kept at 35% by volume. After reaction times of 2 and 3 hours, 35% by volume of ammonia is measured and after 4 and 5 hours 30.5 and 25% by volume respectively are measured. At the end of the reaction time, after 5½ hours, the circulating gas still contains 15% by volume of ammonia. Up to this time, 13.6 l of off-gas, which contain 0.181 mole of ammonia, are withdrawn continuously from the apparatus. Furthermore, 6.9 g of water of reaction containing a further 0.061 mole of ammonia are obtained. Finally, a further 0.029 mole of $NH_3$ are collected when the apparatus is flushed. The total amine yield is 95.3% by weight with an amine number of 31.85. This amine contains 3.1 mole % of primary amine, 92.2 mole % of secondary amine and 4.7 mole % of tertiary amine.

EXAMPLE 4

110 g=0.719 mole of decane nitrile (corresponding to 55.8 mole % of nitrile in the mixture), 90.0 g=0.570 mole of decyl alcohol and 10.0 g of a supported nickel catalyst (5% by weight based on the mixture; 55% of nickel) are initially introduced into the circulation apparatus described in Example 1.

The amount of circulating gas is adjusted to 500 l/kg·hour, the apparatus is warmed to 180° C. and the batch is run at this temperature for 4½ hours, 36.4 l of hydrogen being passed in during this time. The circulating gas contains 5% by volume of ammonia when the reaction temperature is reached and contains 20% by volume after 1 hour and 30% by volume after 3 hours. Off-gas is not withdrawn. The ammonia concentration then falls to 18% by volume after 3 hours and to 6% by volume after 4 hours. At the end of the reaction time, after 4½ hours, 3% by volume of ammonia are still determined. 11.3 g of water of reaction, which contain 0.065 mole of ammonia, are formed and a further 0.011 mole of ammonia are collected when the apparatus is flushed. The total amine yield is 97.4% by weight with an amine number of 31.47. Of the total yield, 0.1 mole % is primary amine, 91.0 mole % is secondary didecylamine and 8.9 mole % is tertiary tridecylamine.

EXAMPLE 5

48.0 g=0.314 mole of decane nitrile, 152.0 g=0.962 mole of decyl alcohol and 10.0 g of a nickel catalyst on a support (5% by weight based on the mixture; 55% of nickel) are initially introduced into the circulation apparatus described in Example 1.

The amount of circulating gas is 500 l/kg·hour, the reaction temperature is 180° C. and the reaction time is 4½ hours. During this time, 15.4 l of hydrogen are continuously supplied and, at the same time, from a cooling trap, 8.0 g=0.471 mole of ammonia are supplied in the course of 3¼ hours, as a result of which the ammonia concentration adjusts to between 30 and 50% by volume during the entire reaction time. Off-gas is not withdrawn. 19.5 g of water of reaction which contains 0.147 mole of ammonia are collected in the water separator and a further 0.048 mole of ammonia are collected when the apparatus is flushed. The crude product obtained after separating off the catalyst contains 99.4% by weight of total amine with an amine number of 32.05. This product contains 0.1 mole % of primary amine, 90.3 mole % of secondary amine and 9.6 mole % of tertiary amine.

EXAMPLE 6

99.5 g=0.65 mole of decane nitrile (corresponding to 50 mole % of nitrile in the mixture), 119.6 g=0.65 mole of an octyl alcohol which has been oxethylated with 1 mole of ethylene oxide (boiling point$_{10}$ 120° to 125° C.) and 10.0 g of a nickel catalyst on a support (5% by weight based on the mixture; 55% of nickel) are initially introduced into the circulation apparatus described in Example 1.

The amount of circulating gas is 500 l/kg·hour, the reaction temperature is 180° C. and the reaction time is 5½ hours. During this time, 32.9 l of hydrogen are continuously supplied. After heating, the circulating gas initially contains 7% by volume of ammonia and after ½ hour contains 25% by volume, after 1 hour 33% by volume and after 2 hours 35% by volume of ammonia, without additional ammonia being supplied. The ammonia concentration in the circulating gas then falls again and at the end of the reaction time is still 3% by volume. 13.0 g of water of reaction containing a further 0.034 mole of ammonia are obtained. The crude product obtained after separating off catalyst contains 95.8% by weight of total amine with an amine number of 30.2. The determination shows that this product contains 84.0 mole % of secondary amine, 16.0 mole % of tertiary amine and no primary amine, and in the secondary amine (boiling point$_{13}$ 212°–218° C.), all 3 possible species can be detected by gas chromatography.

EXAMPLE 7

107.0 g=0.476 mole of dodecyl cyanomethyl ether (corresponding to 52.4 mole % of nitrile in the mixture), 93.0 g=0.433 mole of myristyl alcohol and 5.7 g of a water-moist Raney nickel with a nickel content of 70% by weight, corresponding to 2% by weight of nickel based on the reaction mixture, are initially introduced into the circulation apparatus described in Example 1. The nitrile employed and the alcohol employed are approximately 97% pure according to analysis by gas chromatography.

The amount of circulating gas is 500 l/kg·hour, the reaction temperature is 190° C. and the reaction time is 6¼ hours. After the apparatus has been filled with hydrogen after flushing with nitrogen, it is first heated to 140° C. and gaseous ammonia is then fed in in a proportion of 10% of the volume of circulating gas. During the entire reaction time, that is to say after reaching 190° C., a total of 24.1 l of hydrogen are fed in. Rapid enrichment of ammonia takes place in the cycle. The ammonia concentration is 27% by volume immediately after the reaction temperature is reached and is 60% by volume after a reaction time of ½ hour and 67% by volume after 1 hour. The ammonia concentration in the circulating gas then falls again, to 43% by volume after 1½ hours, to 19% by volume after 2 hours and to 2.9% by volume at the end of the reaction time. No off-gas is withdrawn. 8.2 g of water of reaction containing 0.013 mole of NH$_3$ are collected in the water separator, which is heated to 90° C. A further 0.012 mole of NH$_3$ are discharged during the final flushing of the apparatus. After the catalyst has been separated off, a crude product is obtained which contains 94.5% by weight of total amine with an amine number of 21.08. This consists to the extent of 0.4 mole % of primary amine, to the extent of 88.3 mole % of secondary amine and to the extent of 11.3 mole % of tertiary amine, and in the secondary amines all 3 possible species can be detected by gas chromatography.

EXAMPLE 8

105.0 g=0.394 mole of tallow fatty nitrile (iodine number 57, N content 5.25% by the Kjeldahl method), 95.0 g=0.362 mole of completely hydrogenated tallow fatty alcohol (OH number 214) and 5.7 g of water-moist Raney nickel with a nickel content of 70% by weight, corresponding to 2% by weight of nickel based on the reaction mixture, are initially introduced into the circulation apparatus described in Example 1.

The amount of circulating gas is 500 l/kg·hour. After filling the apparatus with hydrogen, the mixture is heated to 200° C. with vigorous stirring. Gaseous ammonia is fed in at a temperature of 140° C. in an amount comprising 10% of the volume of circulating gas. The reaction time is 2½ hours at a temperature of 200° C. and during this time 22.1 l of hydrogen are fed continuously into the cycle. The ammonia concentration is 42% by volume at the start of the reaction and falls to 33% by volume after ½ hour, to 18% by volume after 1 hour and to 11% by volume at the end of the reaction. During this time, 7.2 g of water which contain 0.005 mole of ammonia are collected in the water separator, which is heated to 90° C. After this reaction has ended, a crude product results which contains 98% by weight of total amine with an iodine number of 20 and an amine number of 19.2; this amine consists to the extent of 4.3 mole % of primary amine, to the extent of 93.1 mole % of secondary amine and to the extent of 2.6 mole % of tertiary amine. This product is further treated for 3 hours at 200° C. in a circulating gas which has previously been free from ammonia by passing through dilute sulfuric acid. During this time, a further 3.9 l of hydrogen are passed in. The iodine number falls to 6 after 1 hour, to 2 after 2 hours and to 1 after 3 hours. The amine now obtained has an amine number of 19.09; it is free from primary amine and contains 95.3 mole % of secondary amine and 4.7 mole % of tertiary amine.

EXAMPLE 9

100.0 g=0.382 mole of tallow fatty nitrile (iodine number 55, nitrogen content by the Kjeldahl method 5.35%), 100.0 g=0.381 mole of hydrogenated tallow fatty alcohol (OH number 214) and 5.7 g of a water-moist Raney nickel with a nickel content of 70%, corresponding to 2% based on the reaction mixture, are initially introduced into the circulation apparatus described in Example 1.

The amount of circulating gas is 500 l/kg·hour, the reaction temperature is 200° C. and the reaction time is 5½ hours. During heating, gaseous ammonia is again fed, at 140° C., in an amount of about 10% of the volume of the circulating gas, into the cycle, and in addition hydrogen is passed in continuously. The circulating gas contains 40% by volume of ammonia at the start of the reaction, 24% by volume of ammonia after ½ hour, 11% by volume of ammonia after 1 hour and less than 4% by volume of ammonia at the end of the reaction. At this time, a total amine is present in a yield of 96.8% by volume; this amine has an iodine number of 15 and an amine number of 18.93. It consists to the extent of 3.2 mole % of primary amine, to the extent of 92.3 mole % of secondary amine and to the extent of 4.5 mole % of tertiary amine. The circulating gas is then run for a further 3 hours at 200° C. without ammonia being withdrawn. The supply of hydrogen is continued, so that the total amount of hydrogen passed in is 24.7 l in all. During this time, the ammonia concentration increases again and after 3 hours is 7.4% by volume. The iodine number decreases and after 3 hours is 2. After a total reaction time of 5¼ hours, a total amine finally results which has an amine number of 18.93 and contains 1.0 mole % of primary amine, 92.7 mole % of secondary amine and 6.3 mole % of tertiary amine.

EXAMPLE 10

150.0 g=0.573 mole of tallow fatty nitrile (iodine number 55, N content by the Kjeldahl method 5.35%), 50.0 g=0.191 mole of hydrogenated tallow fatty alcohol (OH number 214) and 11.7 g of a water-moist Raney nickel with a 70% nickel content, corresponding to 4% by weight based on the reaction mixture, are initially introduced into the circulation apparatus described in Example 1.

The amount of circulating gas is 500 l/kg·hour and the reaction time at 200° C. is 2½ hours. During this time, 32.2 l of hydroggen are passed into the cycle. Ammonia is rapidly enriched in the cycle and therefore part of the circulating gas is passed, in a secondary cycle, through dilute H₂SO₄ in order to keep the ammonia concentration in the circulating gas between 35 and 50% by volume. 0.102 mole of ammonia is determined in the sulfuric acid, and the water of reaction (6.5 g) contains a further 0.009 mole of ammonia. After this reaction time, a total amine results, in a yield of 97.9% by weight, which has an amine number of 19.64 and consists of 7.2 mole % of primary amine, 90.9 mole % of secondary amine and 1.9 mole % of tertiary amine (iodine number 26). The circulating gas is then passed over dilute sulfuric acid for a further one hour and a further 0.097 mole of ammonia are obtained; furthermore, an additional 4.2 l of hydrogen are fed in during this time; additional water of reaction does not form. After this time, an amine results which has a residual iodine number of 4 and an amine number of 18.31, is free from primary amine and consists to the extent of 97.6 mole % of secondary amine; the remainder is tertiary amine.

EXAMPLE 11

50.0 g=0.191 mole of tallow fatty nitrile (iodine number 55, nitrogen content by the Kjeldahl method 5.35%), 150.0 g=0.572 mole of hydrogenated tallow fatty alcohol (OH number 214) and 5.7 g of water-moist Raney nickel with a nickel content of 70% by weight, corresponding to a proportion of Raney nickel of 2% by weight based on the reaction mixture, are initially introduced into the circulation apparatus described in Example 1.

The amount of circulating gas is 500 l/kg·hour and the reaction temperature is 200° C. During the reaction time, 10.5 l of hydrogen are fed continuously into the cycle and, in addition, after a temperature of 140° C. has been reached, 4.25 g=0.241 mole of ammonia are introduced, from a cold trap, into the cycle in the course of 1¼ hours. During the time the ammonia is fed in, the ammonia concentration in the circulating gas is between 30 and 40% by volume; it then falls until it is 8% by volume at the end of the reaction time, after 2½ hours. After this time, a total amine results, in a yield of 97.1% by weight, which has an iodine number of 10 and an amine number of 19.07. This total amine contains 3.9 mole % of primary amine, 91.7 mole % of secondary amine and 4.5 mole % of tertiary amine. The circulating gas is then circulated for a further 1 hour at 200° C. and, during this time, is passed through dilute sulfuric acid in order to remove the ammonia. A further 1.4 l of hydrogen are passed in during this time. Finally, an amine results which has a residual iodine number of 3 and an amine number of 18.92 and which contains 1.3 mole % of primary amine, 93.3 mole % of secondary amine and 5.4 mole % of tertiary amine.

EXAMPLE 12

92.5 g=0.355 mole of stearyl nitrile (nitrogen content by the Kjeldahl method 5.3%), 107.5 g=0.333 mole of behenyl alcohol (OH number 174) and 5.7 g of water-moist Raney nickel with a nickel content of 70%, corresponding to 2% by weight based on the reaction mixture, are initially introduced into the circulation apparatus described in Example 1.

The amount of circulating gas is adjusted to 500 l/kg·hour and the mixture is heated to 200° C.; the reaction time is 3.5 hours. During the heating, gaseous ammonia is introduced into the cycle at 140° C., in an amount of 10% of the volume of circulating gas. During the reaction time, 18 l of hydrogen are fed into the cycle.

The ammonia concentration is 39% by volume when the reaction temperature of 200° C. is reached, 28% by volume after ½ hour, 15% by volume after 1 hour and 3% by volume at the end of the reaction time. A total amine results, in a yield of 97.2% by weight, which has an amine number of 16.79 and consists of 1 mole % of primary amine, 94.3 mole % of secondary amine and 4.7 mole % of tertiary amine.

EXAMPLE 13

105.0 g=0.401 mole of tallow fatty nitrile (iodine number 55, nitrogen content by the Kjeldahl method 5.35%), 95.0 g=0.362 mole of hydrogenated tallow fatty alcohol (OH number 212) and 17.2 of water-moist Raney cobalt with a cobalt content of about 70% by weight, corresponding to 6% by weight of cobalt based on the reaction mixture, are initially introduced into the circulation apparatus described in Example 1.

After the apparatus has been filled with hydrogen, the flow of circulating gas is adjusted to 500 l/kg·hour and the mixture is heated to 180° C., with vigorous stirring. At a temperature of 140° C., gaseous ammonia is fed into the cycle in an amount of 10% of the volume of circulating gas. The reaction time is 8 hours and during this time 22.3 l of hydrogen are fed in. The concentration of ammonia in the circulating gas is 13% by volume immediately after the reaction temperature is reached, 35% by volume after 2.5 hours, 21% by volume after 5 hours and 5% by volume at the end. A total amine results, in a yield of 94.0%, which has an iodine number of 20 and an amine number of 17.97 and consists to the extent of 11.9 mole % of primary amine, to the extent of 86.4 mole % of secondary amine and to the extent of 1.8 mole % of tertiary amine.

EXAMPLE 14

105.0 g=0.401 mole of tallow fatty nitrile (iodine number 55, nitrogen content by the Kjeldahl method 5.35%), 95.0 g=0.362 mole of hydrogenated tallow fatty alcohol (OH number 214) and 4 g of a copper chromite catalyst, corresponding to 2% by weight based on the reaction mixture, are initially introduced into the circulation apparatus described in Example 1.

The amount of circulating gas is 500 l/kg·hour, the reaction temperature is 250° C. and the reaction time is 7 hours. At 140° C., ammonia is added in an amount of 10% of the volume of circulating gas. Furthermore, 20.9 l of hydrogen are fed in during the reaction time. The ammonia concentration increases slowly; it is 25% by volume after 4.5 hours and then decreases slowly again down to 13% by volume at the end of the reaction. A total amine is obtained, in 88.5% yield, which has an iodine number of 27 and an amine number of 16.38. This amine consists to the extent of 10 mole % of primary amine, to the extent of 82.3 mole % of secondary amine and to the extent of 7.7 mole % of tertiary amine.

EXAMPLE 15

Corresponding to Example 6, octane nitrile and tetraethylene glycol mono-n-butyl ether are reacted in the circulation apparatus for 8 hours at 200° C. The amount of circulating gas is 500 l/kg·hour. The ammonia level in the circulating gas is 46% by volume at the start of the reaction and falls to 5% by volume towards the end of the reaction. 93.3% by weight of total amine with an amine number of 24.85 is obtained. Of this total amine, 3.7 mole % is primary amine, 80.5 mole % is secondary amine and 15.8 mole % is tertiary amine.

147.4 g of this total amine are subjected to fractional distillation under a pressure of 9 mm Hg and the following fractions are obtained

| Top temperature (°C.) | Weight (g) |
|---|---|
| 70 to 162 | 16.7 |
| 162 to 165 | 14.1 |
| 165 to 232 | 17.6 |
| 232 to 236 | 38.5 |
| 236 to 275 | 19.9 |
| 275 to 281 | 28.5 |
| residue | 6.0 |
| cold trap | 1.8 |
|  | 143.1 g |

According to analysis by gas chromatography, the fraction which passes over at a top temperature of 232 to 236° C. contains 95.0% by weight of the compound $C_8H_{17}-NH-(CH_2CH_2O)_4-C_4H_9$. The analysis by gas chromatography is carried out in a 1.5 m high column 2 mm in diameter, provided with a packing of 5% by weight of "Silicon Fluid QF$_1$" on "Chromosorg G-AW-DMCS" (obtainable from Messrs. Merck AG, Darmstadt); carrier gas flow: 20 ml/minute of nitrogen; temperature progression: 80° to 250° C. increasing at a rate of 2° C. per minute; sample volume: 0.2 μl.

We claim:

1. In a process for the manufacture of secondary aliphatic amines from aliphatic nitriles and aliphatic alcohols in the liquid phase in the presence of hydrogenation-dehydrogenation catalysts as elevated temperatures and removing water by passing hydrogen gas through the reaction mixture of alcohols and nitriles by contacting at temperatures of from about 120 to about 260° C. and under conditions of virtually atmospheric pressure a primary or secondary aliphatic alcohol of the formula $R_1OH$, wherein $R_1$ is a straight-chain or branced alkyl, alkenyl or ethylenically multi-unsaturated hydrocarbon radial having from 8 to 26 C atoms, or a radical of the formula $R_2(OX)_m-$ having a molecular weight of at least 130, wherein $R_2$ is an alkyl, alkenyl or ethylenically multi-unsaturated hydrocarbon radical having from 1 to 26 C atoms, m is a number of from 1 to 20, X is an alkylene radical selected from the group $-CH_2CH_2-$, $-CH(CH_3)-CH_2-$, or $-CH_2-CH(CH_3)-$ including combinations thereof, or mixtures of said alcohols $R_1OH$, with an aliphatic nitrile of the formula $R_3-CN$, wherein $R_3$ is an alkyl, alkenyl or ethylenically multi-unsaturated hydrocarbon radical having from 8 to 26 C atoms or a radical of the formula $R_4(OX)_n-O(CH_2)_p-$ having a molecular weight of at least 130, wherein $R_4$ is an alkyl, alkenyl or ethylenically multi-unsaturated hydrocarbon radical having from 1 to 26 C atoms, n is a number of from 1 to 20 or 0, p is 1 or 3, X is a radical as defined above including combinations thereof, or mixtures of said nitriles $R_3-CN$ in a molar ratio of alcohol: nitrile of from 90:10 to 10:90, passing and recycling at least 2 moles of hydrogen per mole of said nitrile through the reaction mixture, the improvement which comprises maintaining an ammonia concentration of from 3 to 75% by volume, calculated on the sum of hydrogen and ammonia in the circulating gas, during the entire reaction period.

2. The process as claimed in claim 1, which comprises maintaining the ammonia concentration of from 3 to 60% by volume.

3. The process as claimed in claim 1, wherein the molar ratio of alcohol:nitrile is 70:30 to 30:70.

4. The process as claimed in claim 1, which comprises adding inert gas in an amount of up to 50% by volume, calculated on the sum of hydrogen and ammonia.

5. The process as claimed in claim 1, which comprises contacting alcohols of the formula $R_1OH$, $R_1$ having 16 to 22 C atoms.

6. The process as claimed in claim 1, which comprises contacting nitriles of the formula $R_3-CN$, $R_3$ having 16 to 22 C atoms.

7. The process as claimed in claim 1, which comprises contacting primary alcohols of the formula $R_1OH$, $R_1$ having 14–22 C atoms.

8. The process as claimed in claim 1, which comprises contacting nitriles of the formula $R_3-CN$, $R_3$ having 14–22 C atoms.

* * * * *